United States Patent [19]

Kouzuki

[11] Patent Number: 5,150,037
[45] Date of Patent: Sep. 22, 1992

[54] PARTICLE DETECTOR AND PARTICLE DETECTING APPARATUS HAVING THE DETECTOR

[75] Inventor: Chihiro Kouzuki, Kasaishi, Japan

[73] Assignee: Toa Medical Electronics Co., Ltd., Kobe, Japan

[21] Appl. No.: 757,705

[22] Filed: Sep. 11, 1991

[30] Foreign Application Priority Data

Nov. 30, 1990 [JP] Japan .................. 2-340798

[51] Int. Cl.$^5$ ............ G01N 15/00; G01N 27/07
[52] U.S. Cl. .................. 324/71.4; 324/446; 137/806; 137/13; 73/865.5
[58] Field of Search .......... 137/13, 806, 807; 73/865.5; 324/71.4, 71.1, 439, 449, 447, 446

[56] References Cited

U.S. PATENT DOCUMENTS

| | | | |
|---|---|---|---|
| 3,779,279 | 12/1973 | Schon | 324/71.4 |
| 4,237,416 | 12/1980 | Zold | 324/71.4 |
| 4,284,496 | 8/1981 | Newton | 324/71.4 |
| 4,891,575 | 1/1990 | Kogo | 324/71.4 |

FOREIGN PATENT DOCUMENTS 2750447 5/1979 Fed. Rep. of Germany ..... 73/865.5

*Primary Examiner*—Kenneth A. Wieder
*Assistant Examiner*—Jose M. Solis
*Attorney, Agent, or Firm*—Morrison Law Firm

[57] ABSTRACT

A particle detector is designed to detect particles such as cells and blood corpuscles, and this particle detector includes means for passing and recovering a multilayer flow consisting of an inner layer A of conductive liquid specimen, a middle layer B of conductive first sheath liquid, and an outer layer C of nonconductive second sheath liquid surrounding them, in an orifice 12, and a pair of electrodes disposed on both sides of the orifice so as to contact the conductive liquid respectively. A detector circuit 44 is connected to the pair of electrodes so as to detect a particle signal on the basis of difference of electric impedance between the electrodes. The diameter of the orifice 12 is substantially the diameter of the middle layer. By varying the flow rate balance of the conductive liquids and nonconductive liquid, the diameter of the middle layer may be freely changed. Accordingly, the diameter of the orifice may be apparently changed as desired.

8 Claims, 5 Drawing Sheets

PARTICLE DETECTOR AND PARTICLE DETECTING APPARATUS HAVING THE DETECTOR

BACKGROUND OF THE INVENTION

The present invention relates to a particle detector and particle detecting apparatus having the detector for detecting and analyzing particles by passing particles of cells, blood corpuscles or the like through an orifice in a sheath flow.

A particle detecting apparatus disposing a pair of electrodes across an orifice (aperture) for detecting particles individually on the basis of changes of electric impedance caused when particles pass through the orifice is known well. Also known well is a particle detecting apparatus for forming a sheath flow, and passing the particles in neat order in the center of its orifice. In this case the term "sheath flow" means a flow of a suspension of particles of which surrounded an covered by a laminar flow liquid (sheath liquid), in order to pass particles precisely and neatly in one row in the middle of the orifice.

In such a particle detecting apparatus, the inside diameter of the orifice is, as a matter of course, unchanged, and the size of measurable particles is limited. For example, when measuring large particles, problems of clogging or loss of linearity (linear correlation) occur between the size of particles and magnitude of detection signal, or when measuring small particles, a sufficient S/N ratio is not obtained, and signals are concealed by noise and cannot be detected. By raising the detection current, the S/N ratio may be raised somewhat, but it may result in adverse effects on particles or lead to other problems. The S/N ratio is the ratio of the desired signal to the noise mixed in the signal, and the higher the S/N ratio, the easier it is to detect signals.

The measure from small particles without problems to large particles, it is necessary to vary the size of the orifice depending on the particle size. That is, in the case of large particles, it is necessary to measure with a wider orifice diameter, and in the case of small particles, a narrower orifice diameter is desired. However, since the orifice is assembled into the detector in one body, to vary the orifice diameter, it is necessary to prepare a plurality of detectors having different orifice diameters, and exchange the detector in assembly depending on the particles to be measured.

If the diameter of the orifice is variable, the measuring range of particles may be extended. In the conventional apparatus, this took time because the detectors were exchanged. Further, the orifice diameter could not be varied freely. If the orifice diameter is freely variable, it may be possible to measure particles of any size under optimum conditions, which represents a great progress for in particle measurement.

OBJECTS AND SUMMARY OF THE INVENTION

It is hence a primary object of the invention to present a particle detector wide in a particle measuring range, capable of varying the particle detecting region depending on the purpose, that is, freely varying the size of the orifice substantially without the labor of exchanging the detector or the like, and a particle detecting apparatus having the same detector.

To achieve the above object, in a preferred embodiment, the invention presents a particle detector for passing a liquid specimen suspending particles into an orifice so as to surround the liquid specimen with a sheath liquid, and detecting particles individually depending on the changes based of the electric impedance of liquid and particles, which comprises means for passing and recovering a multilayer flow consisting of a conductive liquid specimen as inner layer, a conductive first sheath liquid as middle layer, and a nonconductive second sheath liquid surrounding them as an outer layer, through an orifice, and a pair of electrodes disposed at both sides of the orifice so as to contact with the conductive liquid.

Meanwhile, the means for passing and recovering the multilayer flow through the orifice comprises a liquid specimen outlet pipe disposed at the upstream side of the liquid from the orifice, a first sheath liquid outlet pipe disposed concentrically on the outer side of the liquid specimen outlet pipe, a first recovery pipe disposed at the downstream side of the liquid from the orifice, and a second recovery pipe disposed concentrically on the outer circumference of this first recovery pipe.

Moreover, instead of the first recovery pipe and second recovery pipe, only one recovery pipe may be disposed.

Besides, the first sheath liquid outlet pipe and first recovery pipe may be composed of conductive material to form electrodes.

The invention also presents, in a different preferred embodiment, a particle detecting apparatus for passing a liquid specimen containing suspended particles into an orifice so as to surround the liquid specimen with a sheath liquid, and detecting particles individually depending on the changes in the electric impedance of liquid and particles, which comprises means for passing and recovering a multilayer flow consisting of a conductive liquid specimen as inner layer, a conductive first sheath liquid as middle layer, and a nonconductive second sheath liquid surrounding them as an outer layer, through an orifice, a pair of electrodes disposed at both sides of the orifice so as to make contact with the conductive liquid, and a detector circuit connected to this pair of electrodes for detecting a particle signal on the basis of the electric impedance between the electrodes.

Meanwhile, the means for passing and recovering the multilayer flow through the orifice comprises a liquid specimen outlet pipe disposed at the upstream side of the liquid from the orifice, a first sheath liquid outlet pipe disposed concentrically on the outer side of the liquid specimen outlet pipe, a first recovery pipe disposed at the downstream side of the liquid from the orifice, a second recovery pipe disposed concentrically on the outer circumference of this first recovery pipe, and liquid specimen supply means, first sheath liquid supply means and second sheath liquid supply means respectively connected to the liquid specimen outlet pipe, first sheath liquid outlet pipe, and the first sheath liquid outlet pipe.

Instead of the first recovery pipe and second recovery pipe, only one recovery pipe may be used.

Still further, the first sheath liquid outlet pipe and first recovery pipe are composed of a conductive material to form electrodes.

In the present invention, as the conductive first sheath liquid, for example, physiological saline or the like is used, and as the nonconductive second sheath liquid, for example, purified water or ethyl alcohol is used.

When the orifice is cylindrical, the inside diameter of the orifice is assumed to be d. The outside diameter of the inner layer (liquid specimen flow) in the orifice is assumed to be a, the outside diameter of the middle layer (conductive liquid flow) to be b, and the outside diameter of the outer layer (nonconductive liquid flow) to be c (c=d). An electric current flows from one electrode to the other electrode through the conductive liquid portions (inner layer, middle layer). The outer layer is nonconductive, and the current does not flow into this region. Accordingly, the current flows only in the internal region with the diameter b, and the diameter of the orifice is substantially regarded to be b.

By varying the flow rate balance of the conductive liquid and nonconductive liquid, the diameter b of the middle layer may be freely changed. Thus, the effective orifice diameter may be varied as desired.

DETAILED DESCRIPTION OF THE PREFERRED EMBODIMENTS

Figure 1:
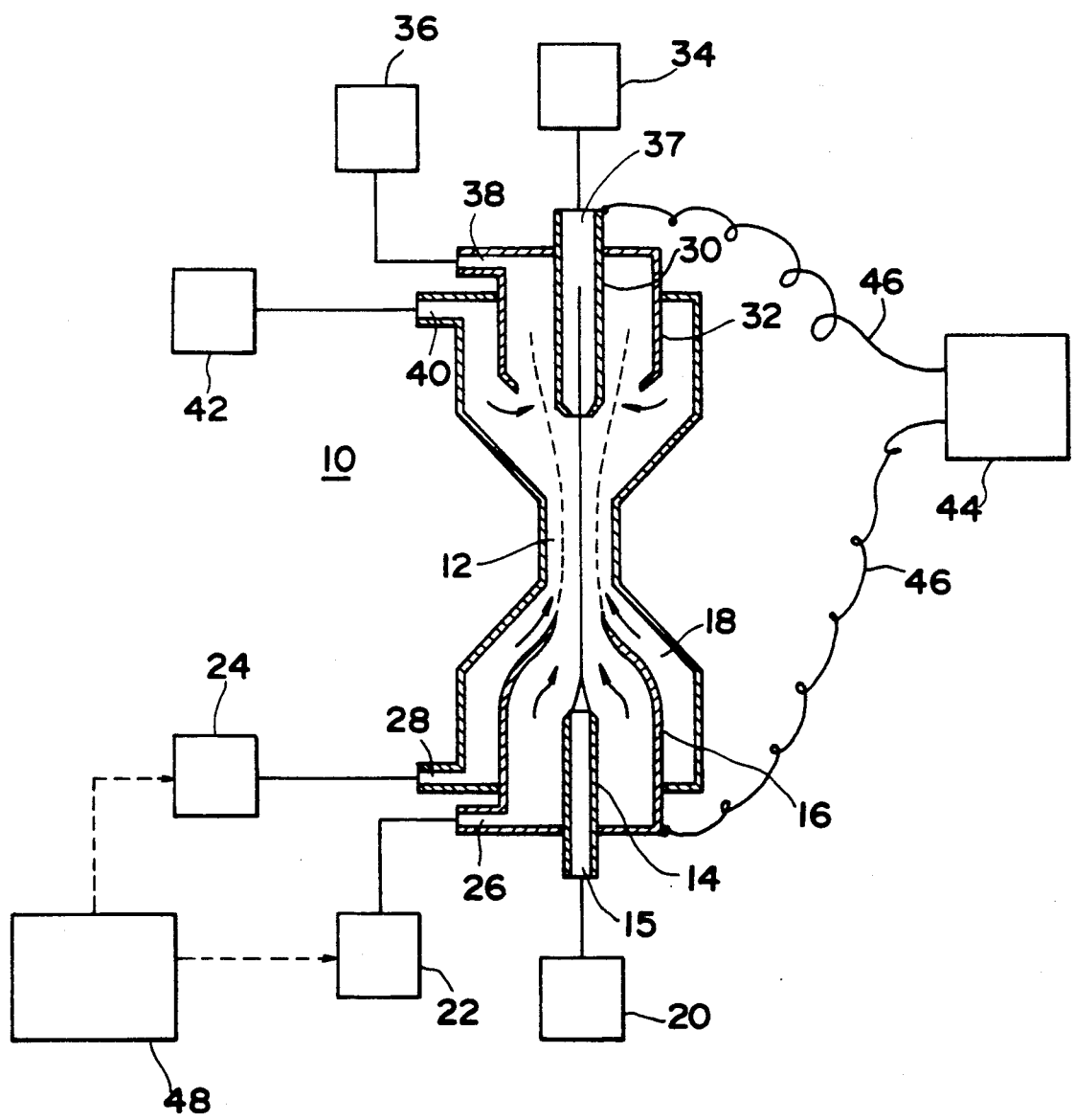
FIG. 1 is a vertical sectional view showing an embodiment around a particle detector of the invention.

Referring now to the drawings, some of the preferred embodiments of the invention are described in detail below.

In FIG. 1, numeral 10 is a detector for passing particles in neat order, and 12 is an orifice (for example, its inside diameter is 100 $\mu$m, and length is 120 $\mu$m). At the upstream side of the orifice 12 (downward in FIG. 1), there is a liquid specimen outlet pipe 14 for discharging a liquid specimen suspending particles, and a first sheath liquid outlet pipe 16 is disposed concentrically outside this liquid specimen outlet pipe 14. The liquid specimen is constantly discharged from liquid specimen supply means 20 (for example, a syringe capable of discharging the liquid at a specific flow rate by a piston) connected to a supply port 15. The front end of the first sheath liquid outlet pipe 16 is located at the downstream side (upward in FIG. 1) of the liquid from the front end of the liquid specimen outlet pipe 14, and, the end of the pipe 16 is tapered. This provides smooth formation of the laminar flow. The first sheath liquid is supplied from the first sheath liquid supply means 22 (syringe or means for pushing out liquid at specific pressure) to a supply port 26 disposed in the lower part of the first sheath liquid outlet pipe 16. The first sheath liquid flows enclosing the surrounding of the liquid specimen. Numeral 18 is a path for the second sheath liquid.

In the present invention, a second sheath liquid may flow outside of the first sheath liquid. The second sheath is a nonconductive liquid. The nonconductive second sheath liquid is supplied into from a supply port 28 disposed in the lower part of the detector 10 from second sheath liquid supply means 24 (syringe or means for pushing out liquid at a specific pressure).

At the downstream side of the orifice 12, a first recovery pipe 30 is provided, and a second recovery pipe 32 is disposed concentrically outside the first recovery pipe 30. In this embodiment, the front end of the second recovery pipe 32 is at the downstream side from the front end of the first recovery pipe 30. Numerals 34, 36 are waste liquid tubs, and the waste liquid tubs 34, 36 are respectively connected to the outlet 37 of the first recovery pipe 30 and the outlet 38 above the second recovery pipe 32. Numeral 42 is a syringe liquid supply means for back sheath, and it is connected to the inlet 40 above the detector 10.

Figure 2:
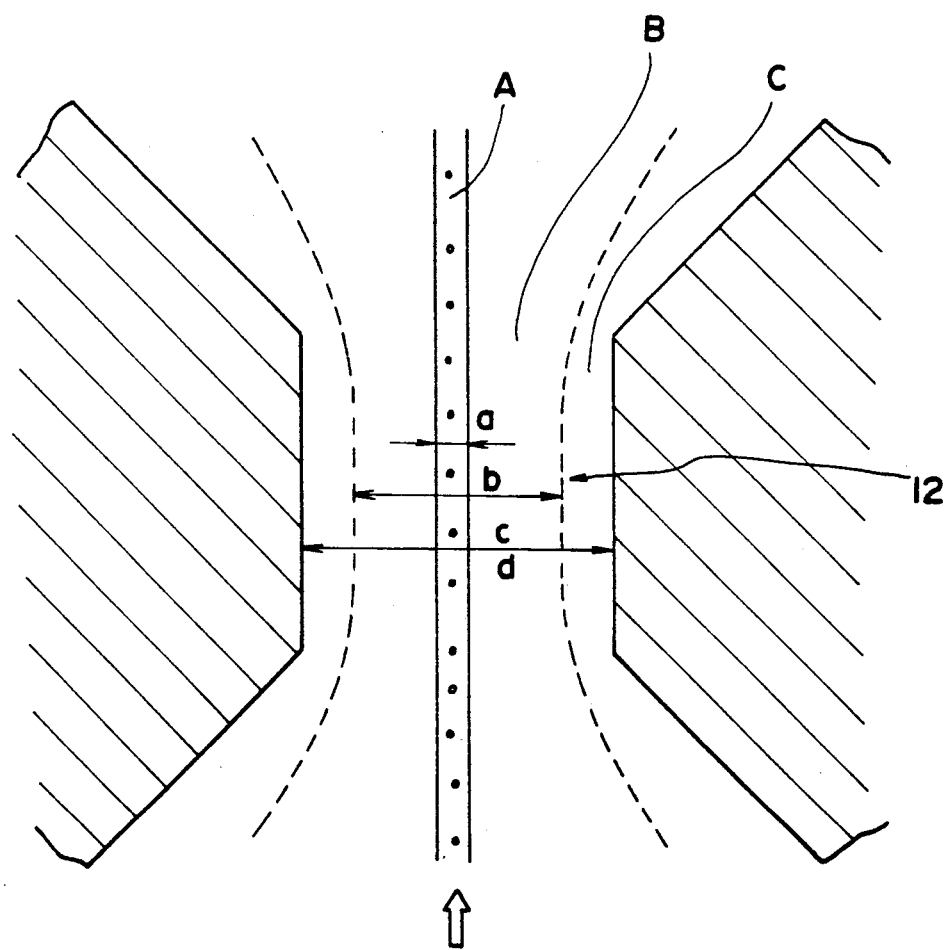
FIG. 2 is a magnified view of the orifice area in FIG. 1.

As shown in FIG. 2, a three-layer flow is formed, consisting of the liquid specimen as inner layer A, first sheath liquid as middle layer B, and second sheath liquid as outer layer C. Being a laminar flow, the liquid of each layer flows without mixing with each other. In the absence of laminar flow, the liquids mix with each other at their boundaries, and particle detection is unstable.

The liquid specimen and first sheath liquid are conductive, and the second sheath liquid is nonconductive. A pair of electrodes are disposed at both sides of the orifice 12 so as to contact the conductive liquid (for example, the first sheath liquid) individually. In this embodiment, the first sheath liquid outlet pipe 16 and the first recovery pipe 30 are composed of conductive material and used as electrodes. More specifically, the first sheath liquid outlet pipe 16 is made of stainless steel and functions as the negative electrode, and the first recovery pipe 30 is made of platinum and functions as the positive electrode. In the first recovery pipe 30, all of the liquid specimens and a part of the first sheath liquid are recovered, and in the second recovery pipe 32, the remainder of the first sheath liquid and all of the second sheath liquid are recovered together with syringe liquid.

Numeral 44 is a detector circuit for supplying a current between the positive electrode 30 and negative electrode 16, and detecting the changes in electric impedance. Numeral 46 is an electric wire. The current flows in the region of the conductive liquid, but does not flow in the region of the nonconductive liquid. Accordingly, by varying the sectional area of the conductive liquid flows (inner layer A and middle layer B) in this three-layer flow, the size of the orifice may be substantially changed. To vary the sectional area of the conductive liquid flows (inner layer A and middle layer B), it is enough to change the flow rate balance of the conductive liquid and nonconductive liquid. This requires at least the means for varying the first sheath liquid supply rate and second sheath liquid supply rate. Numeral 48 is the control means for controlling the liquid supply rate. For obtaining a better laminar flow, it is desirable that the control means 48 also controls the supply rate and discharge rate of other liquid.

What has been described herein relates to a detector such as flow cell of a flow cytometer or the like, but other construction may be also possible.

Figure 3:
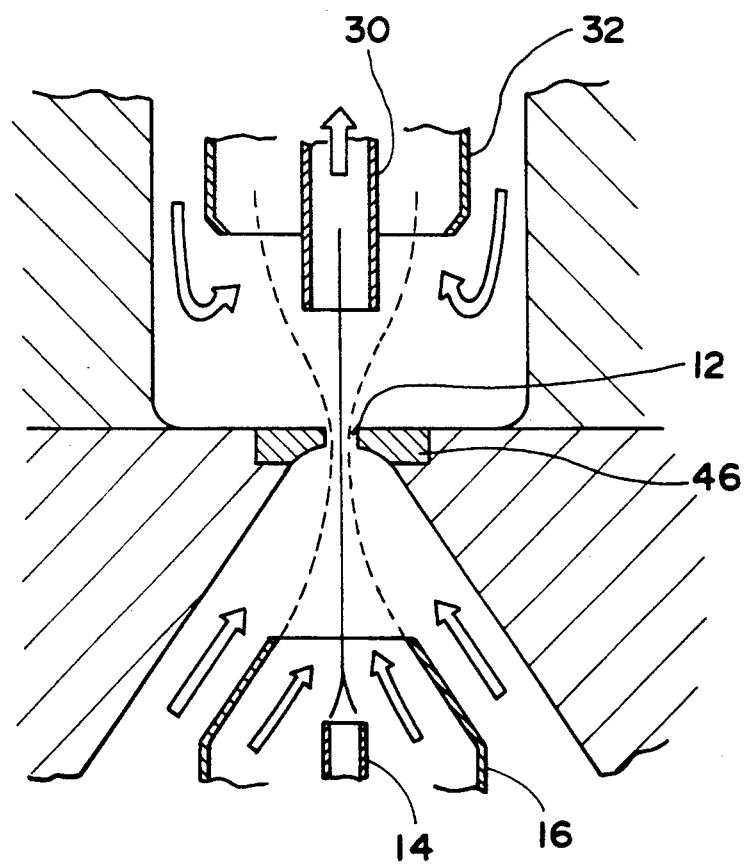
FIG. 3 is sectional view showing another example of the orifice area of the particle detector of the invention.

For example, as shown in FIG. 3, a circular orifice 12 may be formed in the center of a disc-shaped orifice plate 46 made of artificial ruby, ceramic or similar material.

Figure 4:
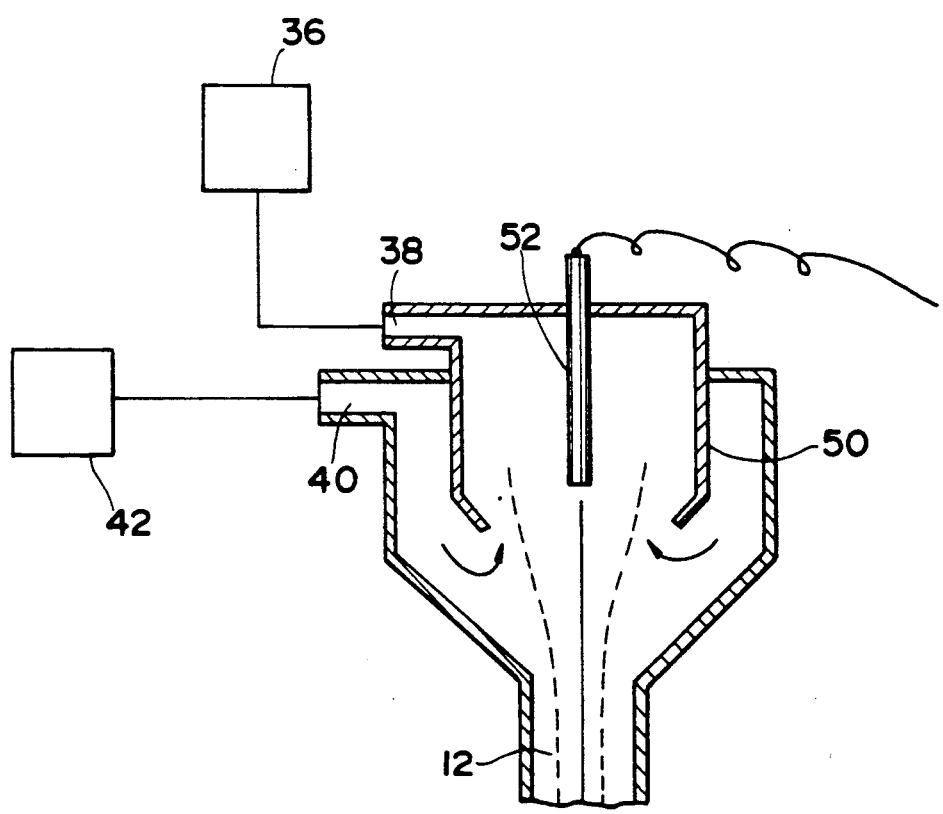
FIG. 4 and FIG. 5 are sectional views showing other embodiments around the recovery pipe of the particle detector of the invention.
Figure 5:
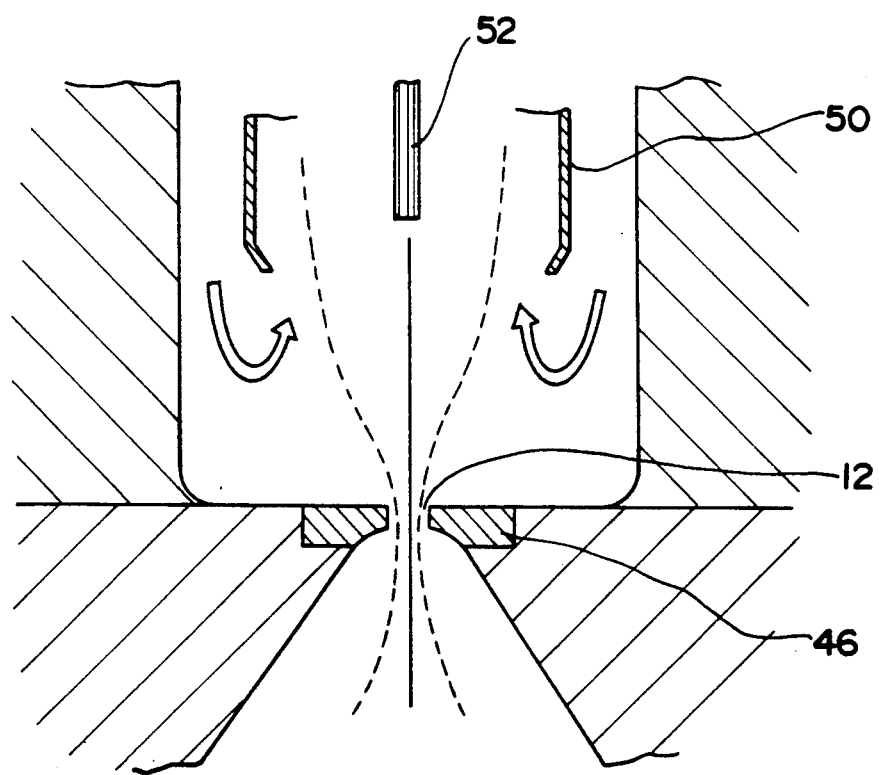

In the embodiment shown in FIGS. 4, 5, instead of the first recovery pipe 30 and second recovery pipe 32 in the foregoing embodiment, a recovery pipe 50 nearly in the same shape as the second recovery pipe is provided, and all of the liquid specimens of inner layer A, first sheath liquid of the middle layer B and second sheath liquid of the outer layer C is recovered in the recovery pipe 50. Inside this recovery pipe 50, a positive electrode 52 is disposed so as to contact the conductive liquid.

The other construction and action are the same as shown in FIGS. 1 to 3.

The invention being thus composed brings about the following effects.

(1) A flow of a nonconductive liquid is formed in the outer layer, and current does not flow in this nonconductive layer, so that the apparent diameter of the orifice (the sectional area) may be smaller. Still further, since the thickness of the nonconductive liquid layer may be freely varied depending on necessity, the diameter of the orifice may be substantially changed.

(2) To vary the diameter of the orifice, it is enough to change the balance of the flowing liquids, and it does not require exchanging the detector or the like. The construction is simple, as well.

(3) Since the diameter of the orifice may be freely changed, the range of measurable particles may be greatly widened. That is, from small particles to large ones, it is always possible to measure in optimum conditions without causing problems such as clogging, noise and lack of linearity (linear correlation).

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A particle detector for passing a liquid specimen suspending particles into an orifice so as to surround the liquid specimen with a sheath liquid, and detecting particles individually depending on the changes based on the difference of the electric impedance of liquid and particles, which comprises means for passing and recovering a multilayer flow consisting of a conductive liquid specimen as inner layer, a conductive first sheath liquid as middle layer, and a nonconductive second sheath liquid surrounding them as outer layer, through an orifice, and a pair of electrodes disposed at both sides of the orifice so as to contact the conductive liquid.

2. A particle detector according to claim 1, wherein the means for passing and recovering the multilayer flow through the orifice comprises a liquid specimen outlet pipe disposed at the upstream side of the liquid from the orifice, a first sheath liquid outlet pipe disposed concentrically on the outer side of the liquid specimen outlet pipe, and at least one recovery pipe.

3. A particle detector according to claim 2, wherein said recovery pipe comprises a first pipe disposed at the downstream side of the liquid from the orifice, and a second pipe disposed concentrically on the outer circumference of said first pipe.

4. A particle detector according to claim 2, wherein the first sheath liquid outlet pipe and said recovery pipe may be composed of conductive material to form electrodes.

5. A particle detecting apparatus for passing a liquid specimen suspending particles into an orifice so as to surround the liquid specimen with a sheath liquid, and detecting particles individually depending on the changes based on the difference of the electric impedance of liquid and particles, which comprises means for passing and recovering a multilayer flow consisting of a conductive liquid specimen as inner layer, a conductive first sheath liquid as middle layer, and a nonconductive second sheath liquid surrounding them as outer layer, through an orifice, a pair of electrodes disposed at both sides of the orifice so as to contact with the conductive liquid, and a detector circuit connected to this pair of electrodes for detecting a parallel signal on the basis of the electric impedance between the electrodes.

6. A particle detector apparatus according to claim 5, wherein the means for passing and recovering the multilayer flow through the orifice comprises a liquid specimen outlet pipe disposed at the upstream side of the liquid from the orifice, a first sheath liquid outlet pipe disposed concentrically on the outer side of the liquid specimen outlet pipe, at least one recovery pipe, and liquid specimen supply means and first sheath liquid supply means, respectively connected to the liquid outlet pipe, and the first sheath liquid outlet pipe.

7. A particle detector apparatus according to claim 6, wherein said recovery pipe comprises a first pipe disposed at the downstream side of the liquid from the orifice, and a second pipe disposed concentrically on the outer circumference to the first pipe.

8. A particle detecting apparatus according to claim 6, wherein the first sheath liquid outlet pipe and said recovery pipe are composed of conductive material to form electrodes.

* * * * *